US010668256B2

(12) United States Patent
Osypka

(10) Patent No.: US 10,668,256 B2
(45) Date of Patent: Jun. 2, 2020

(54) BALLOON DILATION ASSEMBLY

(71) Applicant: Peter Osypka Stiftung, Grenzach-Wyhlen (DE)

(72) Inventor: Peter Osypka, Grenzach-Wyhlen (DE)

(73) Assignee: Peter Osypka Stiftung, Grenzach-Wyhlen (DE)

( * ) Notice: Subject to any disclaimer, the term of this patent is extended or adjusted under 35 U.S.C. 154(b) by 246 days.

(21) Appl. No.: 15/806,761

(22) Filed: Nov. 8, 2017

(65) Prior Publication Data

US 2018/0133443 A1    May 17, 2018

(51) Int. Cl.
*A61M 25/10* (2013.01)
*A61B 17/12* (2006.01)
*A61F 2/01* (2006.01)
*A61M 29/02* (2006.01)
*A61B 17/22* (2006.01)
*A61B 17/00* (2006.01)

(52) U.S. Cl.
CPC ... *A61M 25/1011* (2013.01); *A61B 17/12122* (2013.01); *A61B 17/12136* (2013.01); *A61F 2/013* (2013.01); *A61M 25/1002* (2013.01); *A61M 29/02* (2013.01); *A61B 2017/00783* (2013.01); *A61B 2017/1205* (2013.01); *A61B 2017/12127* (2013.01); *A61B 2017/22055* (2013.01); *A61B 2017/22098* (2013.01); *A61F 2002/016* (2013.01); *A61M 2025/1015* (2013.01); *A61M 2025/1061* (2013.01); *A61M 2025/1088* (2013.01); *A61M 2210/125* (2013.01)

(58) Field of Classification Search
CPC ........ A61B 17/12122; A61B 17/12136; A61B 2017/00783; A61B 2017/1205; A61B 2017/12127; A61B 2017/22055; A61B 2017/22098; A61F 2/013; A61F 2002/016; A61M 25/1002; A61M 25/1011; A61M 29/02; A61M 2025/1015; A61M 2025/1061; A61M 2025/1088; A61M 2210/125
See application file for complete search history.

(56) References Cited

U.S. PATENT DOCUMENTS

| 4,787,388 | A | * | 11/1988 | Hofmann | .......... A61M 25/1002 604/913 |
| 6,068,611 | A | * | 5/2000 | Loffler | .................. A61M 25/10 604/101.02 |
| 2003/0055452 | A1 | * | 3/2003 | Joergensen | ............. A61F 2/013 606/200 |

(Continued)

FOREIGN PATENT DOCUMENTS

| CA | 1305385 C | 7/1992 |
| DE | 102012111984 A1 | 6/2014 |
| EP | 0231725 A1 | 8/1987 |

*Primary Examiner* — Jocelin C Tanner
(74) *Attorney, Agent, or Firm* — Locke Lord LLP; Scott D. Wofsy

(57) ABSTRACT

A balloon dilation assembly for use in balloon valvuloplasty is disclosed, which includes at least three outer balloons arranged around a central balloon and fixed to the central balloon, wherein each balloon has a supply tube for inflation and flow channels are provided between each adjacent pair of outer balloons, whereby at least one of the outer balloons is shorter in length than the remaining outer balloons and the central balloon.

9 Claims, 5 Drawing Sheets

(56) References Cited

U.S. PATENT DOCUMENTS

| | | | |
|---|---|---|---|
| 2004/0249413 A1* | 12/2004 | Allen | A61B 17/00491 |
| | | | 606/214 |
| 2005/0171472 A1* | 8/2005 | Lutter | A61B 17/00234 |
| | | | 604/101.03 |
| 2012/0179033 A1 | 7/2012 | Merhi | |
| 2012/0209375 A1* | 8/2012 | Madrid | A61F 2/2433 |
| | | | 623/2.11 |
| 2013/0150956 A1 | 6/2013 | Yohanan et al. | |

* cited by examiner

BALLOON DILATION ASSEMBLY

CROSS-REFERENCE TO RELATED APPLICATION

This application claims the benefit of priority under 35 U.S.C. § 119 (a) to German Patent Application DE 10 2016 013 480.1 filed with the German Patent Office on Nov. 11, 2016, the disclosure of which is incorporated by reference herein in its entirety.

BACKGROUND OF THE INVENTION

1. Field of the Invention

The present disclosure relates to a balloon dilation assembly for performing balloon valvuloplasty to dilate a stenotic heart valve, and more particularly, to dilate a stenotic aortic valve, and to methods of using a balloon dilation assembly by either a transfemoral approach or a transapical approach.

2. Description of Related Art

Transcatheter aortic valve implantation (TAVI) is a common treatment of aortic stenosis. It is the replacement of the aortic valve of the heart through the blood vessel. In most cases the replacement valve is delivered transfemoral, whereby a balloon catheter is placed in the femoral artery (in the groin) and guided into the heart.

The replacement valve can also be delivered by a transapical approach through the wall of the heart. In this procedure mini-thoracotomy is performed to obtain a straight access to the left ventricular apex. Sutures are first placed to close afterwards the thoracotomy opening. The left ventricle apex is punctured with a standard access needle. A guide wire is inserted into the left ventricle and directed through the aortic valve and to the ascending aorta. Then a trocar is inserted into the left ventricular apex to maintain intraventricular access. The balloon catheter is then guided via the guide wire through the left ventricle to the aortic valve. Aortic balloon valvuloplasty is performed during a brief episode of rapid ventricular pacing. A compressed heart valve is delivered through the trocar and positioned across the aortic annulus. Once in position, the balloon is inflated to secure the valve in place.

The inflated balloon blocks the blood flow. To overcome this problem the European patent publication EP0231725 corresponding to the Canadian patent publication CA1305385 suggests a dilation device having three balloons arranged around a support tube. Upon inflation of the balloons flow channels (so called flow tubes) are formed between the balloons through which blood can flow.

During balloon valvuloplasty dilating forces are generated not only within the aortic valve itself but also within the surrounding tissue where the atrioventricular (AV) node and the HIS bundle lies. The AV node and the HIS bundle are both part of the electrical conduction system of the heart.

The pressure applied to the AV node and the HIS bundle upon inflation of the balloons may disturb the conduction of the electric signals of the sinus node via AV node and HIS bundle into the ventricles so that a block may occur in the electrical conduction system (AV block). In case of an AV block, the patient needs a pacemaker after the replacement of the heart valve.

In order to minimize tissue damage in the area of the AV node it is known to use particularly shaped balloons. The balloon assembly of e.g. the German Patent Publication DE10 2012 111 984 has three circularly cylindrical areas with different diameters, whereby the diameter of the second area is smaller than the diameter of the first and third area.

SUMMARY OF THE INVENTION

The object of the present invention is to minimize the pressure applied to the AV node and to the HIS bundle during balloon valvuloplasty or even to avoid any pressure to the AV node and to the HIS bundle. This is achieved by a balloon dilation assembly comprising at least three outer balloons arranged around a central balloon wherein at least one of the outer balloons is shorter in length compared to the remaining outer balloons and the central balloon.

The invention thus relates to a balloon dilation assembly and to methods of performing balloon valvuloplasty. The assembly comprises at least three outer balloons arranged around a central balloon, whereby each balloon has a supply tube used for inflating the balloon. The outer balloons are arranged in a circle around the central balloon. There are flow channels between each pair of two adjacent outer balloons through which blood can flow.

Each outer balloon is fixed to the central balloon. The outer balloons are distally closed and the closed ends are fixed to the tail end of the supply tube of the central balloon. The outer balloons are preferably in addition fixed, e.g. glued to the central balloon. When the assembly is positioned in the area of the heart valve the at least one short outer balloon is positioned adjacent to the septum, thus providing enough space in the area of the AV node and the HIS bundle so as not to exert pressure against the AV node and the HIS bundle during balloon inflation. The balloons of the assembly are made as known valvuloplasty balloons. The length, diameter and wall thickness of the balloons may vary.

In one embodiment, all outer balloons are shorter in length as compared to the central balloon. Such an assembly is easier to place as it does not make any difference which one of the outer balloons is positioned adjacent to the septum. The number of balloons being present can vary to match the anatomy of the heart valve. A minimum number of three outer balloons should be present for ensuring an even dilation of the stenotic heart valve. A number of three to six balloons is well feasible.

In one embodiment, one of the outer balloons is replaced by two balloons arranged or otherwise longitudinally aligned one after the other. The distance between the two balloons may be fixed or may be variable. The distally placed first balloon lies in use position in the area of the heart valve and is used—like all other outer balloons—to dilate the heart valve. The proximally placed second balloon is used to stabilize the alignment of the balloon catheter assembly. The distally placed first balloon is shorter in length compared to the remaining outer balloons and the central balloon. The distally placed first balloon and the proximally placed second balloon are connected by their common supply tube forming a spacer.

In the use position, the spacer lies in the area of the AV node and the HIS bundle, thus minimizing or even avoiding pressure being applied to said area. By moving the two balloons relative to each other along the longitudinal axis, the spacer can be adjusted with regard to its length.

The inflation of the balloons may be effected in a known manner with a liquid or a gas. The supply tubes to each balloon may be interconnected so that each balloon is inflated simultaneously. The supply tubes to each balloon may also be separate so that each balloon is separately supplied and independently inflated. This is an advantage for providing different dilation forces. The central balloon is guided via the firstly placed guide wire to the aortic valve area.

In one embodiment, the balloon dilation assembly further consists of a protective element in form of a filter or of an occluder. The protective element is fixed to the guidewire at its upper end and is inserted together with the guidewire. The protective element is helpful to catch atherosclerotic plaques during the valve replacement process. The protective element is preferably a self-expandable braiding made of shape memory material, e.g. made of nitinol.

The invention further relates to methods for performing balloon valvuloplasty using the transfemoral approach as well as using the transapical approach. The invention thus relates to a method for performing balloon valvuloplasty using the transfemoral approach comprising the steps of inserting a guidewire through a patient's vasculature and pulling the guidewire through the valve to be dilated; advancing the balloon dilation assembly—as described above—over the guide wire to the valve to be dilated; inflating the balloons by introducing an inflation medium through the supply tubes and dilating the valve to be dilated; deflating the balloons by removing the inflation medium; and removing the balloon catheter from the patient's body.

The invention further relates to a method for performing balloon valvuloplasty using the transapical approach comprising the steps of inserting a guidewire into the heart through a puncture in the myocardium and pulling the guidewire through the valve to be dilated; inserting a trocar with a pre-inserted balloon dilation assembly—as described above—over the guidewire and advancing an valvuloplasty balloon catheter to the valve to be dilated; inflating the balloons by introducing an inflation medium through the supply tubes and dilating the valve to be dilated; deflating the balloons by removing the inflation medium; and removing the balloon catheter from the patient's body.

These and other features of the system and methods of the subject invention will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art will readily understand how to make and use the system and methods of the subject invention without undue experimentation, preferred embodiments thereof will be described in detail herein below with reference to the figures wherein.

DETAILED DESCRIPTION OF THE FIGURES

Figure 1:
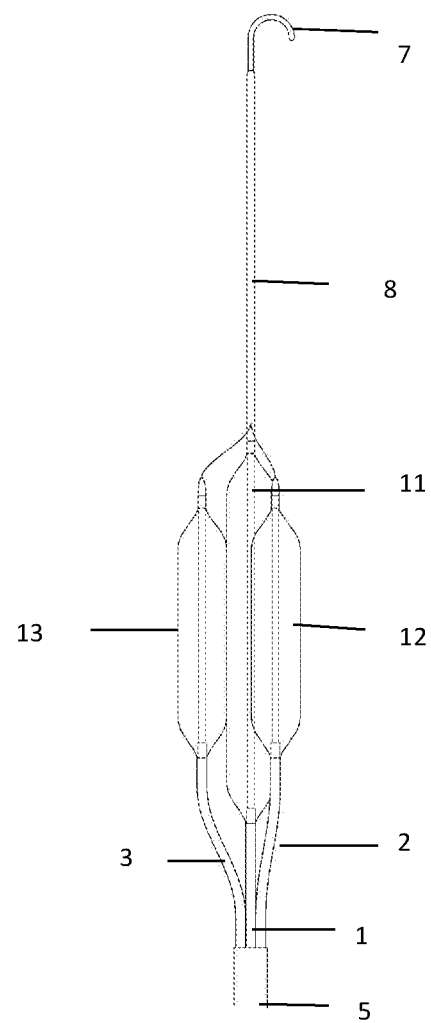
FIG. 1 illustrates a longitudinal section view of the inventive balloon dilation assembly.

Referring now to the drawings wherein like reference numerals identify similar structural elements or features of the subject invention, FIG. 1 illustrates a longitudinal section view of the inventive balloon dilation assembly. The assembly comprises three outer balloons (12, 13, 14) arranged around a central balloon (11). Each balloon can be filled with a liquid or a gas via its supply tube (1, 2, 3, 4) to inflate the balloon. Tube (4) with balloon (14) is located behind the central balloon (11) and is thus not visible.

The supply tubes (1, 2, 3, 4) are coming out of a trocar (5). The outer balloons (12, 13, 14) are arranged in a circle around the central balloon (11). FIG. 1 shows the inflated balloons. Flow channels are generated between each pair of two adjacent balloons. The supply tube (1) of the central balloon (11) has a tail end (8). Through the supply tube of the central balloon plus tail end (8) the guide wire (7) is thrust. Each outer balloon is distally closed and the closed ends are fixed to the tail end (8) of the supply tube (1) of the central balloon (11).

To give the balloon dilation assembly more stability, each outer balloon is glued to the central balloon. The outer balloons (12, 13, 14) are shorter in length as compared to the central balloon (11). This is necessary to minimize or even avoid the pressure to the AV node and the HIS bundle when inflating the balloons. The balloon dilation assembly is placed using guide wire (7) running inside supply tube (1).

Figures 2, 3:
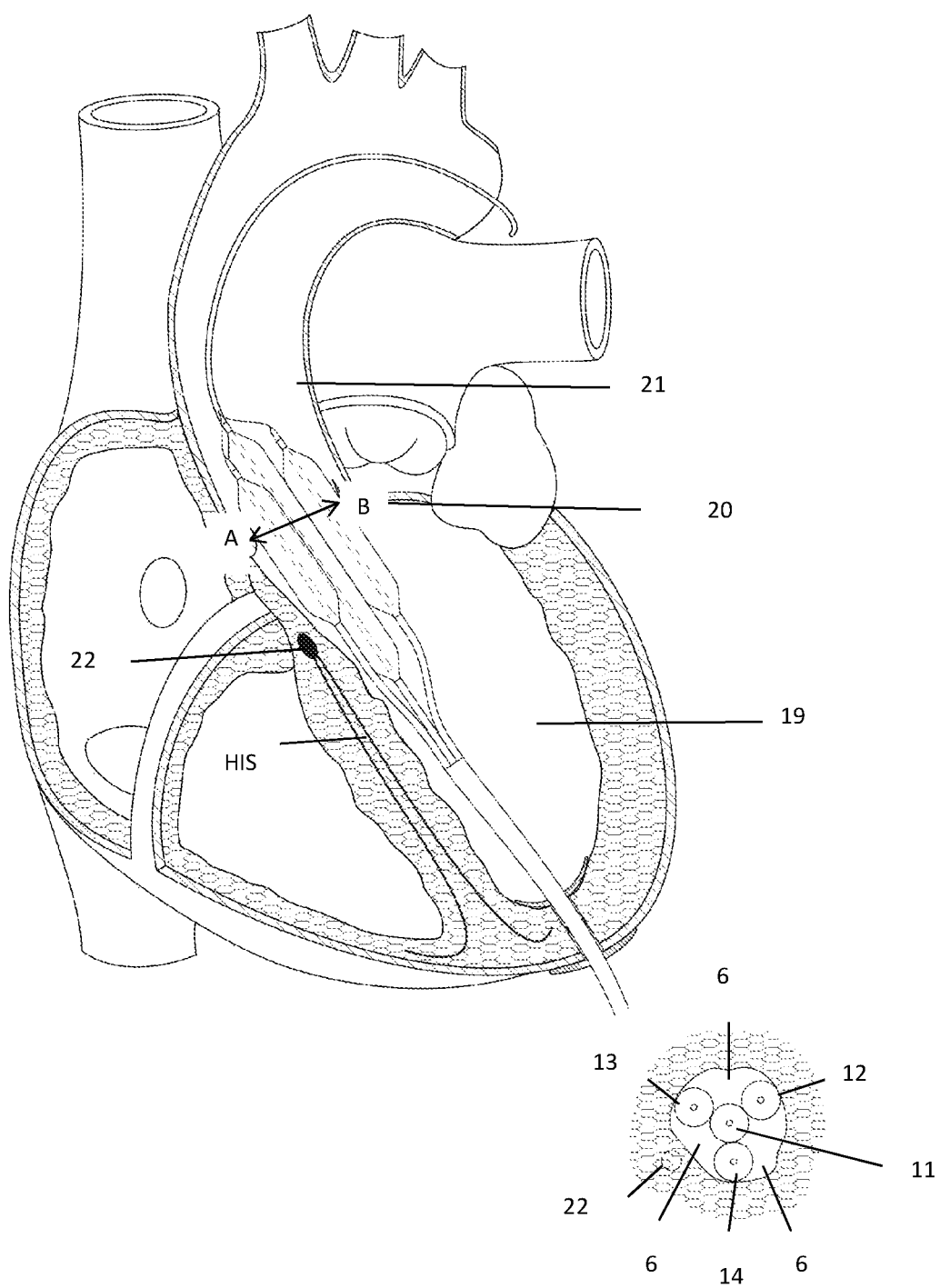
FIG. 2 illustrates a schematic view of the heart with the balloon dilatation assembly according to FIG. 1 being placed.
FIG. 3 is a cross-sectional view of the aortic valve area along line A-B of FIG. 2.

FIG. 2 illustrates a schematic view of the heart with the balloon dilatation assembly according to FIG. 1 being placed. The assembly is used in a transapical approach of performing aortic balloon valvuloplasty. Using guide wire (7) the balloon dilation assembly has been guided through the left ventricle (19), fed to the aortic valve (20) and further to the ascending aorta (21). The balloons have been inflated.

The AV node (22) is marked with the black dot. The AV node is located in the heart septum beneath the aortic valve. The outer balloons (12, 13, 14) press against the aortic valve along the line A-B thus dilating the aortic valve (20). The outer balloons (12, 23, 14) are arranged symmetrically in a circle around the central balloon (11). Flow channels run lengthwise along the balloons between each pair of two adjacent outer balloons. The outer balloons are shorter in length as compared to the central balloon. FIG. 2 shows that the area around the AV node and the HIS bundle is exposed to less pressure compared to the pressure applied to the aortic valve.

Referring to FIG. 3, there is shown a cross-sectional view of the aortic valve area taken along line A-B of FIG. 2. Here, the outer balloons (12, 13, 14) are arranged symmetrically in a circle around the central balloon (11). Three flow channels (6) are generated between each pair of two adjacent outer balloons. In the cross-sectional plane, the flow channels (6) form an open segment of about 60 degree (⅙ of the cross sectional plane circumference) provided that the diameter of each balloon corresponds to the diameter of the flow channel. The AV node is marked by a dashed circle because the AV node (22) is beneath the cross-sectional plane A-B. It can be seen that the AV node is not under pressure due to the fact that the outer balloons are shorter than the central balloon.

Figure 4:
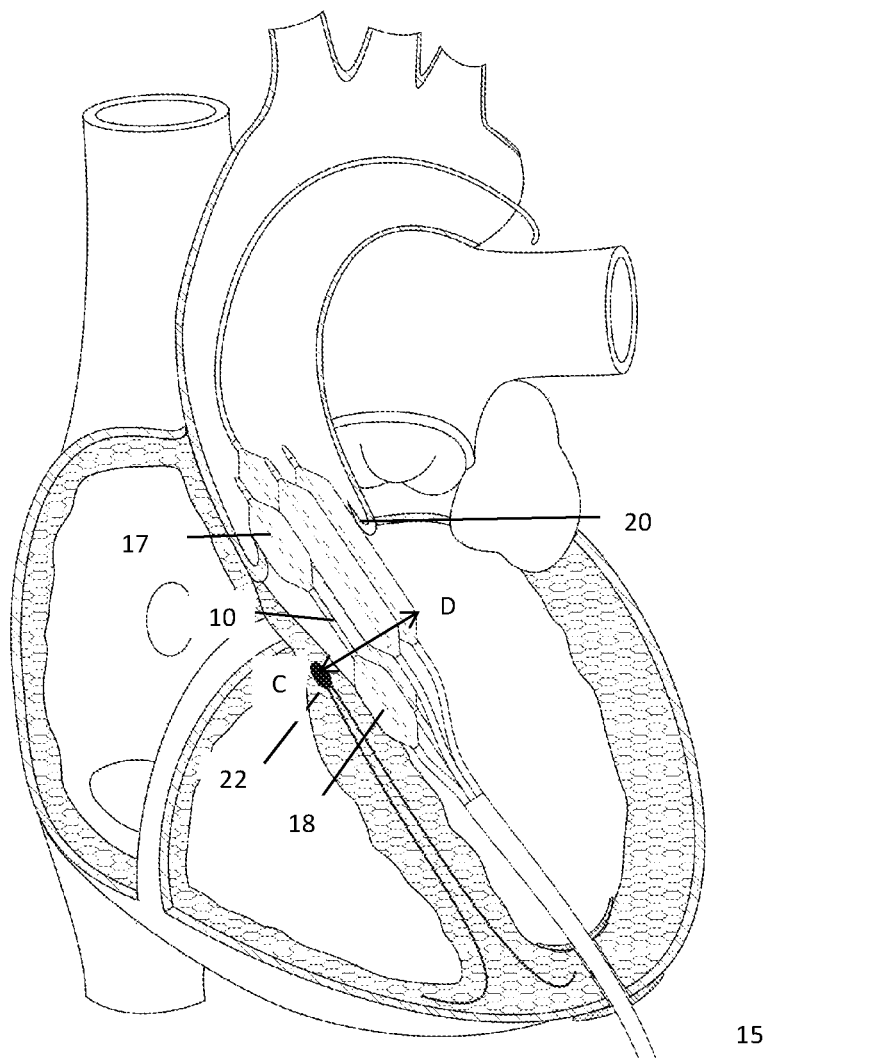
FIG. 4 illustrates a schematic view of the heart as FIG. 2 does.

FIG. 4 illustrates a schematic view of the heart as shown in FIG. 2. A balloon dilatation assembly as shown in FIG. 1 has been inserted. The reference numerals are the same as used in FIGS. 1 and 2. In contrast to the balloon dilation assembly illustrated in FIG. 2, six outer balloons are arranged around the central balloon. One of the outer balloons (designated as balloon 17, 18) consists of two balloons arranged or otherwise longitudinally aligned one after the other. Balloon (17) is distally placed; while balloon (18) is proximally placed.

Balloon (17) is used to dilate the aortic valve like the other outer balloons. Balloon (18) is used to stabilize the alignment of the balloon catheter assembly. Balloon (17) and balloon (18) are interconnected by their common supply tube forming a spacer (10). It is shown that the spacer lies in the area of the AV node (22) and the HIS bundle, thus minimizing or avoiding pressure to the tissue in the AV node area. Balloon (18) is movable along the spacer (10) thus allowing to adjust the length of the spacer.

Figure 5:
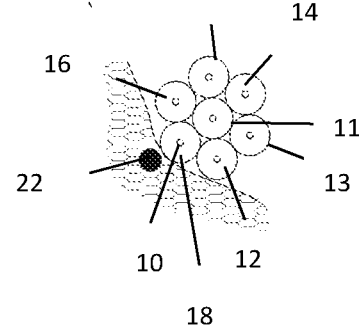
FIG. 5 is a cross-sectional view along line C-D of FIG. 4.

Referring to FIG. 5, there is shown a cross-sectional view taken along line C-D of FIG. 4. Line C-D runs in line with the AV node (22) being marked as black dot. There is no pressure to the AV node as only spacer (10) lies in the same plane as the AV node. The circle around spacer (10) signs the subjacent level where balloon (18) is placed.

Figure 6:
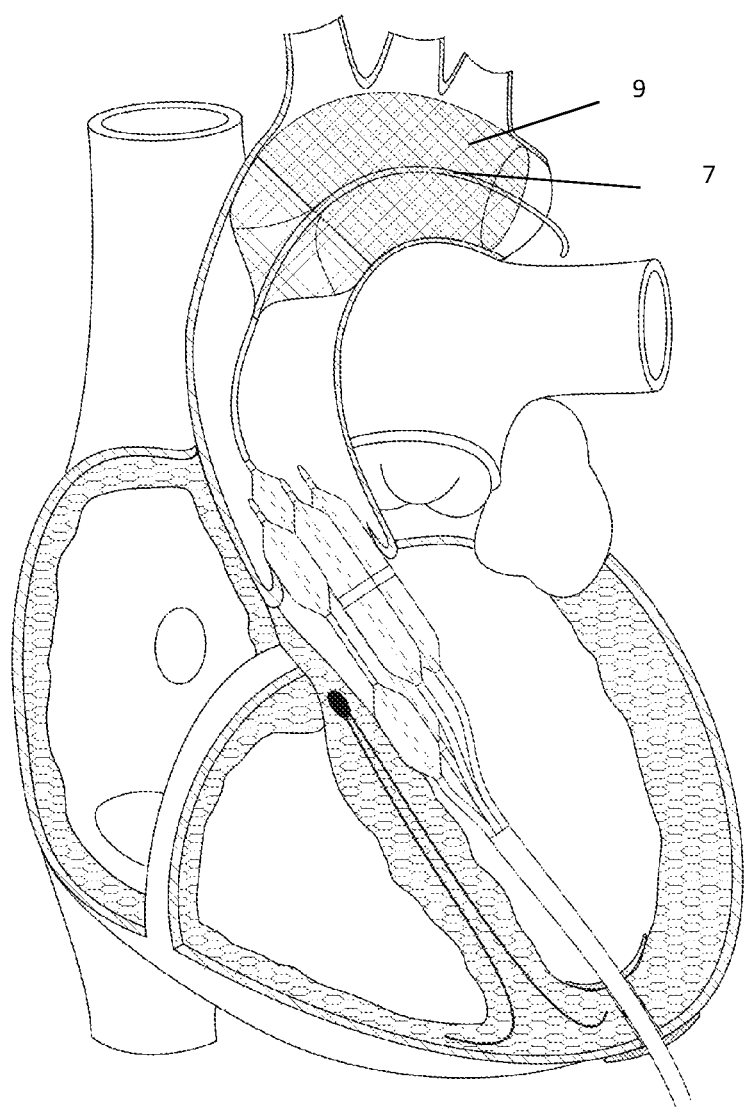
FIG. 6 illustrates the balloon dilation assembly according to FIG. 4.

FIG. 6 illustrates the balloon dilation assembly according to FIG. 4. A self-expandable braiding (9) made of nitinol is shown in its expanded configuration. The braiding is placed in the upper part of the guide wire (7) in the area of the aortic arch and is helpful to catch atherosclerotic plaques during the balloon valvuloplasty procedure.

Figure 7:
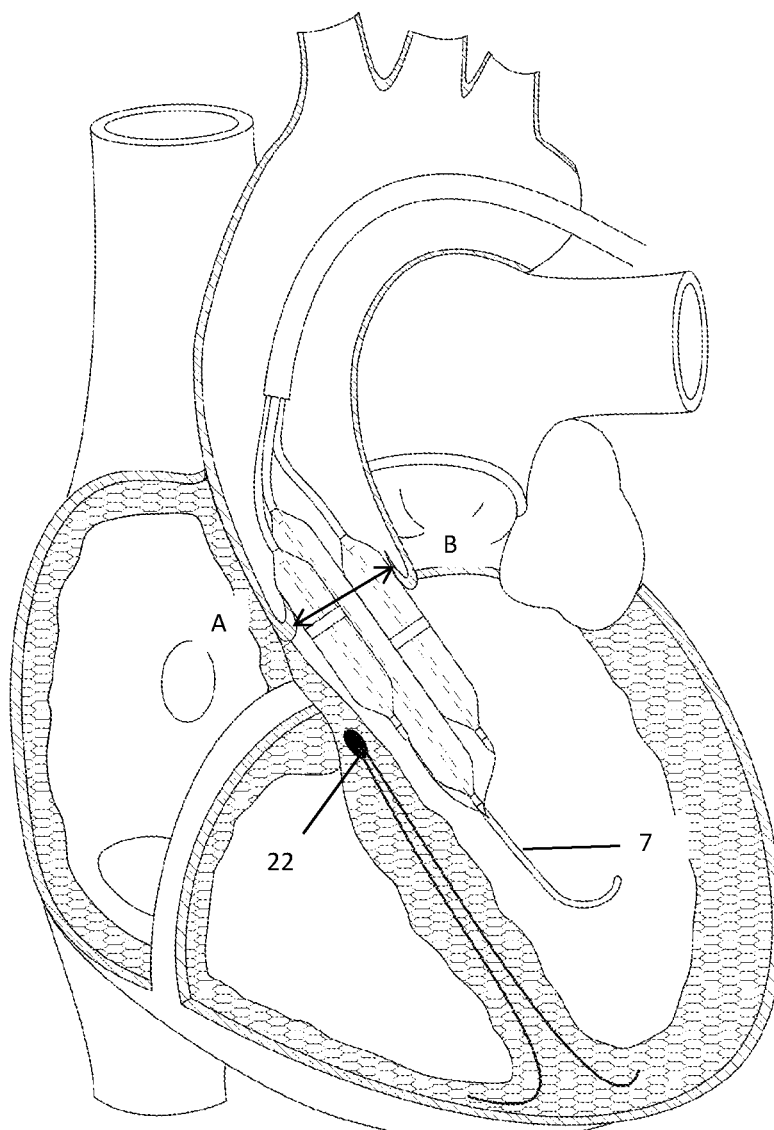
FIG. 7 illustrates a schematic view of the heart with the balloon dilatation assembly according to FIG. 1 being placed.

Referring now to FIG. 7, there is illustrated a schematic view of the heart with the balloon dilatation assembly according to FIG. 1 being placed. The assembly is used in a transfemoral approach of performing aortic balloon valvuloplasty. Using guide wire (7), the assembly has been guided through the femoral artery, fed to the aortic valve and further to the left ventricle. The balloons have been inflated.

Figure 8:
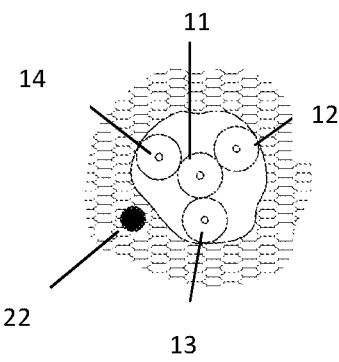
FIG. 8 shows that the area around the AV node.

The AV node (22) is marked with the black dot. The outer balloons (12, 13, 14) press against the aortic valve along the line A-B, thus dilating the aortic valve, as shown in FIG. 2. The outer balloons are shorter in length compared to the central balloon. The outer balloons (12, 23, 14) are arranged symmetrically in a circle around the central balloon (11), as shown in FIG. 8. Flow channels are provided between each pair of two adjacent outer balloons. FIG. 8 shows that the area around the AV node and the HIS bundle is exposed to less pressure as compared to the pressure applied to the aortic valve.

While the subject disclosure has been shown and described with reference to preferred embodiments, those skilled in the art will readily appreciate that changes and/or modifications may be made thereto without departing from the scope of the subject disclosure.

What is claimed is:

1. A balloon dilation assembly for use in balloon valvuloplasty comprising:
  at least three outer balloons arranged around a central balloon and fixed thereto, wherein each balloon has a supply tube for inflation and flow channels are provided between each adjacent pair of outer balloons, whereby at least one of the outer balloons is shorter in length than the other outer balloons and the central balloon, wherein one of the outer balloons is an arrangement of two balloons arranged one after the other and wherein the two balloons are movable relative to each other along a longitudinal axis of the supply tube connecting the balloons.

2. The balloon dilation assembly according to claim 1, having three to six outer balloons.

3. The balloon dilation assembly according to claim 1, wherein all outer balloons are shorter in length than the central balloon.

4. The balloon dilation assembly according to claim 1, further comprising a guidewire for placing the balloon dilation assembly by way of the supply tube of the central balloon, wherein a protective element in form of a filter is fixed to an upper end of the guidewire for placement in an area of a heart's aortic arch in a use position.

5. The balloon dilation assembly according to claim 1, further comprising a guidewire for placing the balloon dilation assembly by way of the supply tube of the central balloon, wherein a protective element in form of an occluder is fixed to an upper end of the guidewire for placement in an area of a heart's aortic arch in a use position.

6. A method of performing balloon valvuloplasty using a transapical approach comprising the steps of:
  a) providing a balloon dilation assembly having at least three outer balloons arranged around a central balloon and fixed thereto;
  b) inserting a guidewire into the heart through a puncture in the myocardium and pulling the guidewire through a valve to be dilated;
  c) inserting a trocar with a pre-inserted balloon dilation assembly over the guidewire and advancing the balloon dilation assembly to the valve to be dilated;
  d) inflating the balloons by introducing an inflation medium through supply tubes and dilating the valve to be dilated;
  e) deflating the balloons by removing the inflation medium; and
  f) removing the balloon dilation assembly from the patient's body.

7. The method of claim 6, wherein the step of inflating the balloons involves the simultaneous inflation of the balloons.

8. The method of claim 6, wherein the step of inflating the balloons involves the separate inflation of each balloon independently.

9. The method of claim 6, further comprising the step of inserting a protective element together with the guidewire to catch atherosclerotic plaques during valve replacement.

* * * * *